US010675760B2

(12) United States Patent
Whitman et al.

(10) Patent No.: US 10,675,760 B2
(45) Date of Patent: Jun. 9, 2020

(54) ROBOT IDENTIFICATION MANAGER

(71) Applicant: International Business Machines Corporation, Armonk, NY (US)

(72) Inventors: Todd R. Whitman, Bethany, CT (US); Aaron K. Baughman, Silver Spring, MD (US); David Bastian, Addison, IL (US); Nicholas McCrory, Sacramento, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/008,107

(22) Filed: Jun. 14, 2018

(65) Prior Publication Data

US 2019/0381664 A1 Dec. 19, 2019

(51) Int. Cl.
*B25J 13/00* (2006.01)
*B25J 9/16* (2006.01)

(52) U.S. Cl.
CPC ........... *B25J 9/1674* (2013.01); *B25J 9/1694* (2013.01)

(58) Field of Classification Search
CPC ..... B25J 9/1697; G06Q 20/40; G06Q 20/401; G06Q 20/4012; G06Q 50/28; H04W 12/06; H04W 12/08; H04W 4/70; H04W 4/80

(Continued)

(56) References Cited

U.S. PATENT DOCUMENTS 5,343,554 A 8/1994 Koza et al.
8,670,868 B2 * 3/2014 Emmertz ........... G05B 19/0426
700/245

(Continued)

FOREIGN PATENT DOCUMENTS

WO 2014146085 A1 9/2014
WO 2016187002 A1 11/2016
WO 2017070269 A1 4/2017

OTHER PUBLICATIONS

"Knowledge Based Systems in Training and Diagnostics", An IP.com Prior Art Database Technical Disclosure, Disclosed Anonymously, IP.com No. IPCOM000218571D, Electronic Publication Date Jun. 5, 2012, 22 pages. http://ip.com/IPCOM/000218571D.

(Continued)

*Primary Examiner* — Dalena Tran
(74) *Attorney, Agent, or Firm* — Michael A. Petrocelli

(57) ABSTRACT

Aspects of the present invention disclose a method, computer program product, and system for identifying a robotic. The method includes receiving an authentication request for an unknown robotic device asserting to be a first robotic device. The method further includes receiving a first identification dataset for the first robotic device. The method further includes issuing an identification action to the unknown robotic device. The method further includes generating a second identification dataset for the unknown robotic device based upon a response to the identification action received from the unknown robotic device. The method further includes in response to determining the first identification dataset matches the second identification dataset, determining that the unknown robotic device is the first robotic device. The method further includes authenticating the unknown robotic device in response to determining that the unknown robotic device is the first robotic device.

25 Claims, 4 Drawing Sheets

(58) Field of Classification Search
USPC ......... 700/245, 259; 340/5.2, 5.8, 5.81–5.83, 340/5.85
See application file for complete search history.

(56) References Cited

U.S. PATENT DOCUMENTS

| | | | |
|---|---|---|---|
| 8,968,195 | B2 | 3/2015 | Tran |
| 9,221,177 | B2 | 12/2015 | Herr et al. |
| 9,676,097 | B1* | 6/2017 | Gallagher ................ B25J 9/161 |
| 9,908,239 | B1* | 3/2018 | O'Brien ..................... B25J 9/02 |
| 2013/0310979 | A1 | 11/2013 | Herr et al. |
| 2014/0194702 | A1 | 7/2014 | Tran |
| 2017/0282375 | A1* | 10/2017 | Erhart .................. B25J 11/0015 |
| 2018/0161982 | A1* | 6/2018 | Bugenhagen ...... G06K 9/00885 |
| 2019/0010750 | A1* | 1/2019 | Scanu .................. G05D 1/0011 |

OTHER PUBLICATIONS

"System, Method or Apparatus for Exchanging Knowledge, Information, Products or any Entity(ies) of Value, and Real Time Market and/or Individual Sensitive or Responsive System of Education", Disclosed Anonymously, IP.com No. IPCOM000177786D, Electronic Publication Date Jan. 1, 2009, http://ip.com/IPCOM/000177786D.

Lepora, et al.; "Tactile Quality Control with Biomimetic Active Touch", IEEE Robotics and Automation Letters, vol. 1, No. 2, Jul. 2016, pp. 646-652.

Lepora, et al. "Tactile Superresolution and Biomimetic Hyperacuity" IEEE Transactions on Robotics, vol. 31, No. 3, Jun. 2015, 14 pages.

Potts et al, "Proof of concept development and motion verification of a swimming anguilliform robot (NEELBOT-1.0)", Proceedings of the 2013 Grand Challenges on Modeling and Simulation Conference, Toronto, Ontario, Canada—Jul. 7-10, 2013, ISBN: 978-1-62748-275-2, 10 pages.

Schmidt et al., "Incorporating expert knowledge in evolutionary search: a study of seeding methods", Proceedings of the 11th Annual conference on Genetic and Evolutionary Computation Conference, (GECCO) Montreal, Québec, Canada , Jul. 8-12, 2009, © 2009, pp. 1091-1098.

Sun et al., "Active visual tracking of free-swimming robotic fish based on automatic recognition", Proceedings of the 11th World Congress on Intelligent Control and Automation, Jun. 29-Jul. 4, 2014, Shenyang, China, 6 pages.

Medina et al., "Impedance-based Gaussian Processes for predicting human behavior during physical interaction", Proceedings of the 2016 IEEE International Conference on Robotics and Automation (ICRA), May 16-21, 2016, Stockholm, Sweden, 7 pages.

Costa et al., "Tracking and Identifying in Real time the Robots of a F-180 Team" RoboCup-99: Robot Soccer World Cup III. RoboCup 1999. Lecture Notes in Computer Science, vol. 1856, Springer, Berlin, Heidelberg, 6 pages.

The Joint Commission, "The Universal Protocol for Preventing Wrong Site, Wrong Procedure, and Wrong Person Surgery: Guidance for Health Care Professionals", Printed Mar. 10, 2018, <http://www.jointcommision.org/assets/1/18/UP_Poster.pdf>.

International Search Report and Written Opinion, International Application No. PCT/IB2019/054851, International Filing Date Jun. 11, 2019, 9 pages.

* cited by examiner

ROBOT IDENTIFICATION MANAGER

BACKGROUND

The present invention relates generally to the field of cognitive computing and more particularly to robotic security.

Robotics deals with the design, construction, operation, and use of robots, as well as computer systems for their control, sensory feedback, and information processing.

These technologies are used to develop machines that can substitute for humans and replicate human actions. Robots can be used in any situation and for any purpose, but today many are used in dangerous environments (including bomb detection and de-activation), manufacturing processes, or where humans cannot survive. Robots can take on any form but some are made to resemble humans in appearance. This is said to help in the acceptance of a robot in certain replicative behaviors usually performed by people. Such robots attempt to replicate walking, lifting, speech, cognition, and basically anything a human can do. Many of today's robots are inspired by nature, contributing to the field of bio-inspired robotics.

Robotic surgery is a term used for correlated actions of a surgeon and a surgical robot (that has been programmed to carry out certain actions during the preoperative planning procedure). A surgical robot is a mechanical device (generally looking like a robotic arm) that is computer-controlled. Robotic surgery can be divided into three types, depending on the degree of surgeon interaction during the procedure: supervisory-controlled, telesurgical, and shared-control. In a supervisory-controlled system, the procedure is executed solely by the robot, which will perform the pre-programmed actions. A telesurgical system, also known as remote surgery, requires the surgeon to manipulate the robotic arms during the procedure rather than allowing the robotic arms to work from a predetermined program. With shared-control systems, the surgeon carries out the procedure with the use of a robot that offers steady-hand manipulations of the instrument. In most robots, the working mode can be chosen for each separate intervention, depending on the surgical complexity and the particularities of the case.

Remote surgery (also known as telesurgery) is the ability for a doctor to perform surgery on a patient even though they are not physically in the same location. It is a form of telepresence. A robot surgical system generally consists of one or more arms (controlled by the surgeon), a master controller (console), and a sensory system giving feedback to the user. Remote surgery combines elements of robotics, cutting edge communication technology such as high-speed data connections and elements of management information systems. While the field of robotic surgery is fairly well established, most of these robots are controlled by surgeons at the location of the surgery. Remote surgery is essentially advanced telecommuting for surgeons, where the physical distance between the surgeon and the patient is immaterial.

SUMMARY

According to one embodiment of the present invention, a method for identifying a robotic device is provided. The method includes receiving an authentication request for an unknown robotic device asserting to be a first robotic device. The method further includes receiving a first identification dataset for the first robotic device. The method further includes issuing an identification action to the unknown robotic device. The method further includes generating a second identification dataset for the unknown robotic device based upon a response to the identification action received from the unknown robotic device. The method further includes in response to determining the first identification dataset matches the second identification dataset, determining that the unknown robotic device is the first robotic device. The method further includes authenticating the unknown robotic device in response to determining that the unknown robotic device is the first robotic device. The method further includes initiating a request for knowledge priors from the first robotic device, where the knowledge priors relates to previously stored identification results of the first robotic device; receiving, by one or more processors, knowledge priors from the first robotic device. The method further includes determining that the knowledge priors match the knowledge priors on one or more databases; and granting, access to the first robotic device to one or more restricted areas. The method further includes initiating an interrogation of the unknown robotic device asserting to be the first robotic device and interrogating the unknown robotic device asserting to be the first robotic device. The method also includes determining that the unknown robotic device asserting to be the first robotic device responds to the interrogation in a manner that corresponds to data on one or more databases and admitting the first robotic device to one or more restricted areas.

The method utilizes a biomimetic signal identification for robot identification which is advantageous because the present invention utilizes a multi-dimensional method to identify a robotic device. The identification method utilizes a cognitive robotic component regression based priors system to accumulate evidence for the active and passive identification of a robot. The signal identification method utilizes robotic knowledge evidence in combination with biomimetic signal identification to actively and passively identify a robot.

DETAILED DESCRIPTION

Figure 1:
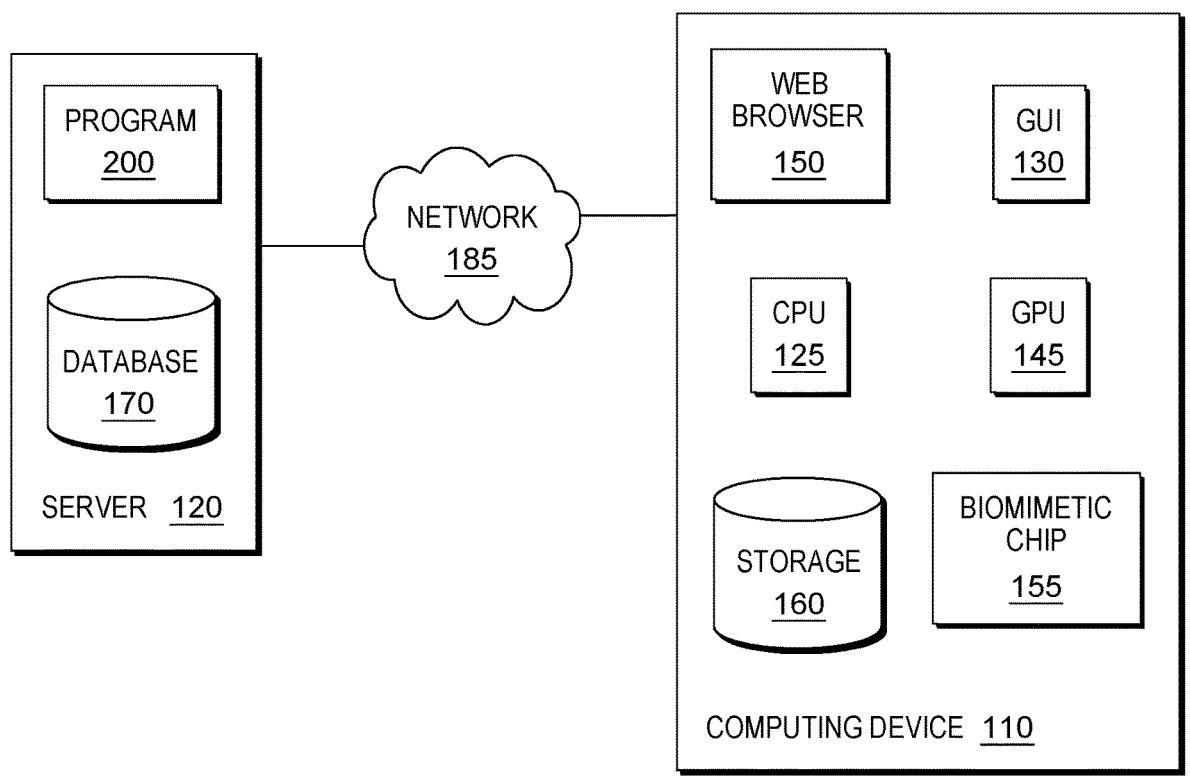
FIG. 1 is a functional block diagram illustrating a distributed data processing environment, in accordance with an embodiment of the present invention.

Embodiments of the present invention recognize that the proliferation of robots introduces unique problems. Various situations, ranging from corporate security to medical matters, will require the ability to positively identify and voir dire a robot to ensure that the robot is the correct robot for the task. The expression "voir dire" is translated to mean "that which is true" and the expression is often related to evidence, competence, and other matters that are associated with bias. In order to ensure corporate security, the identification of robot personnel is as important as the positive identification of human personnel. Robots that lack the proper clearance should no more be allowed into sensitive area than robots' human counterparts.

Embodiments of the present invention recognize that The Joint Commission has established The Universal Protocol to (i) prevent wrong person, (ii) wrong procedure, and (iii) wrong site surgery in hospitals and outpatient settings. In order to ensure patient safety, and to effectively address medical malpractice concerns, the positive identification of a medical surgical robot is paramount. In order for robots to participate in surgeries, the robots will need to be able to comply with The Universal Protocol and thus be able to identify themselves and to state their qualifications for the medical task at hand.

Embodiments of the present invention recognize that current approaches to identify robots are relegated to the use of radio frequency identification devices (RFID). RFID tags are highly susceptible to relay attacks which threaten access control systems. Relay attacks involve the use of an illegitimate tag B as well as a rogue reader. In an example, the original tag A and reader (which is at the restricted area), are some distance apart. The fake reader reads the original tag and uses the information to program tag B with tag A's identifier. Tag B then acts as tag A and communicates with the legitimate reader to obtain illegal access to the restricted area. Embodiments of the present invention also recognize that RFID tags can very easily be counterfeited or copied allowing the impersonation of tags.

Embodiments of the present invention recognize that current approaches to identify robot devices are problematic. Current methods of verifying a robotic device's identity utilize outdated and easily counterfeit-able methods. For example, identifying a robotic device utilizing a MAC address, or only a barcode, or an electromagnetic signature are very easily commandeered by an outside entity. Embodiments of the present invention also recognize that identity is a multi-dimensional construct and that current methods utilize one method, if any, of identifying a robotic device.

Embodiments of the present invention provide a method that utilizes a multi-dimensional identification construct to identify a robotic device. The present invention utilizes a biomimetic signal identification for robot identification which is advantageous because the present invention utilizes a multi-dimensional method to identify a robotic device. The identification method utilizes a cognitive robotic component regression based priors system to accumulate evidence for the active and passive identification of a robot. The signal identification method utilizes robotic knowledge evidence in combination with biomimetic signal identification to actively and passively identify a robot.

Referring now to FIG. 1, shown is a functional block diagram of an example distributed data processing environment in which embodiments of the present disclosure may be implemented. In one embodiment, computing device 110 includes computer processing unit (CPU) 125, graphical user interface (GUI) 130, graphical processing unit (GPU) 145, web browser 150, biomimetic chip 155, and storage 160. The various programs on computing device 110 include a web browser, an electronic mail client, security software (e.g., a firewall program, a geo-locating program, an encryption program, etc.), an instant messaging (IM) application (app), and a communication (e.g., phone) application.

Computing device 110 may be a robotic device, desktop computer, a laptop computer, a tablet computer, a specialized computer server, a smartphone, a wearable device (e.g., smart watch, personal fitness device, personal safety device), or any programmable computer system known in the art with an interactive display or any other computer system known in the art. In certain embodiments, computing device 110 represents a computer system utilizing clustered computers and components that act as a single pool of seamless resources when accessed through network 185, as is common in data centers and with cloud computing applications. In general, computing device 110 is representative of any programmable electronic device or combination of programmable electronic devices capable of executing machine-readable program instructions and communicating with other computer devices via a network.

In one embodiment, Central Processing Unit 125, (CPU) receives data input, executes instructions, and processes information. CPU 125 communicates with Input/Output (I/O) devices, which send and receive data to and from the CPU. Additionally, CPU 125 has an internal bus for communication with the internal cache memory, called the backside bus. The main bus for data transfer to and from the CPU, memory, chipset, and AGP socket is called the front side bus. CPU 125 contains internal memory units, which are called registers. These registers contain data, instructions, counters, and addresses used in the ALU information processing.

In one embodiment, graphical user interface 130 operates on computing device 110. In another embodiment, graphical user interface 130 operates on another computer in a server-based setting; for example, on a server computer (e.g., server 120). In yet another embodiment, graphical user interface 130 operates on computing device 110 simultaneously with a server computer interconnected through network 185 (e.g., server 120). Graphical user interface 130 may be any user interface used to access information from computing device 110, such as information gathered or produced by program 200. Additionally, graphical user interface 130 may be any user interface used to supply information to computing device 110, such as information supplied by a user for input to program 200. In some embodiments, graphical user interface 130 may present a generic web browser used to retrieve, present, and negotiate resources from the Internet. In other embodiments, graphical user interface 130 may be a software or application that enables a user at computing device 110 access to network 185.

In yet another embodiment, a user of computing device 110 can interact with graphical user interface 130 through a touch screen that performs as both an input device to a graphical user interface (GUI) and as an output device (i.e., an electronic display) presenting a plurality of icons associated with software applications or images depicting the executing software application. Optionally, a software application (e.g., a web browser) can generate graphical user interface 130 operating within the GUI of computing device 110. Graphical user interface 130 accepts input from a plurality of input/output (I/O) devices including, but not limited to, a tactile sensor interface (e.g., a touch screen or a touchpad) referred to as a multi-touch display. An I/O device interfacing with graphical user interface 130 may be connected to computing device 110, which may operate utilizing wired (e.g., USB port) or wireless network communications (e.g., infrared, NFC, etc.). Computing device 110 may include components, as depicted and described in further detail with respect to FIG. 4, in accordance with embodiments of the present invention.

Graphics Processing Unit 145, (GPU) is a programmable logic chip (processor) specialized for display functions. In an example, GPU 145 renders images, animations and video for the computer's screen. GPUs are located on plug-in cards, in a chipset on the motherboard or in the same chip as the CPU (not shown). GPU 145 performs parallel operations. Although GPU 145 is used for 2D data as well as for zooming and panning the screen, GPU 145 assists with decoding and rendering of 3D animations and video. The more sophisticated the GPU, the higher the resolution and the faster and smoother the motion in games and movies. GPUs on stand-alone cards include their own random-access memory (RAM), while GPUs in the chipset or CPU chip share main memory with the CPU. GPU 145 has a massively parallel architecture consisting of thousands of smaller, more efficient cores designed for handling multiple tasks simultaneously. GPU 145 lifts the burden from the CPU to free up cycles that could be used for other jobs.

Web browser 150 may be a generic web browser used to retrieve, present, and traverse information resources from the Internet. In some embodiments, web browser 150 may be a web browser designed for a mobile device. In other embodiments, web browser 150 may be a web browser designed for a traditional computing device, such as a desktop computer, PC, or laptop. In general, web browser 150 may be any application or software that enables a user of computing device 110 to access a webpage over network 185. In the depicted environment, web browser 150 resides on computing device 110. In other embodiments, web browser 150, or similar web browsers, may reside on other computing devices capable of accessing a webpage over network 185.

Biomimetic chip 155 contains the weights from one or more neural networks that have been trained to include cognitive movements, and sounds that are used to identify a robot. In one embodiment, Biomimetic chip 155 is located on the robotic device that is being verified. In another embodiment, Biomimetic chip 155 is located on the computing device that is verifying the identification of a robotic device. In another embodiment, Biomimetic chip 155 is located on both devices, the robotic device being verified, and the computing device that is verifying the identification of the robotic device. In an embodiment, biomimetic chip 155 has been trained from a neural network, or cognitive module, that calibrates a robot's sensors to move in a signature way in response to a request or gesture for positive identification. Biomimetic chip 155 has been trained to move and/or make signature sounds that emulate human behaviors to actively and passively identify a robot. In an example, a user instructs a surgical robotic arm to verify that the robotic surgical arm is appropriate for a brain surgery. The robot, through the trained neural network deployed on biomimetic chip 155, located on either or, both, the robotic device and the computing device identifying the robotic device, would initiate a characteristic movement to verify that the robot is the correct robot.

Storage 160 (e.g., a database) located on computing device 110, represents any type of storage device capable of storing data that is accessed and utilized by computing device 110. In other embodiments, storage 160 represents multiple storage devices within computing device 110. Storage 160 stores information such as, but not limited to, account information, credentials for authentication, user preferences, lists of preferred users, previously visited websites, history of visited Wi-Fi portals, and the history of the location of the computing device.

In general, network 185 can be any combination of connections and protocols that will support communications among computing device 110. Network 185 can include, for example, a local area network (LAN), a wide area network (WAN), such as the Internet, a cellular network, or any combination of the preceding, and can further include wired, wireless, and/or fiber optic connections.

Server 120 may be a desktop computer, a laptop computer, a tablet computer, a specialized computer server, a smartphone, or any other computer system known in the art. In certain embodiments, server 120 represents a computer system utilizing clustered computers and components that act as a single pool of seamless resources when accessed through network 185, as is common in data centers and with cloud computing applications. In general, server 120 is representative of any programmable electronic device or combination of programmable electronic devices capable of executing machine-readable program instructions and communicating with other computer devices via a network. In one embodiment, server 120 includes database 170 and program 200.

In an embodiment, server 120 is capable of initiating a handshake process between server 120 and computing device 110. Handshaking is an automated process of negotiation that dynamically sets parameters of a communications channel established between two entities before normal communication over the channel begins. Handshaking follows the physical establishment of the channel and precedes normal information transfer. Handshaking facilitates connecting heterogeneous computing systems, or equipment, over a communication channel without the need for user intervention to set parameters. In an example, server 120 initiates the handshake process by sending a massage to computing device 110 indicating that server 120 wants to establish a communication channel in order to gain access to programs on computing device 110.

Database 170 may be a repository that may be read by server 120. Database 170 represents any type of storage device capable of storing data that is accessed and utilized by server 120. In other embodiments, database 170 represents multiple storage devices within server 120. Database 170 stores information such as, but not limited to, account information, credentials for authentication, user preferences, lists of preferred users, previously visited websites, history of visited Wi-Fi portals, and the history of the computing devices, and information located on the computing devices, that access the server, telephone call, video conference, or live conversation between one or more users.

In one embodiment, program 200 operates on server 120. In another embodiment, program 200 operates on another computer in a server-based setting, for example on a server computer not shown. In yet another embodiment, program 200 operates on computing device 110 simultaneously with server 120 interconnected through network 185. Program 200 provides the capability to detect and mitigate adversarial conversations with virtual agents. Program 200 is capable of utilizing Wi-Fi technology, Bluetooth, Near Field Communication tags (NFC), Global System for Mobile Communications (GSM), and Global Positioning System Technology (GPS) to communicate with computing device 110.

In an example embodiment, program 200 operates as a code snippet within one or more applications on computing device 110. Code snippets define the scope of interactivity between the snippets and the application, (e.g., program 200 hosted by a web browser application on server 120). For example, program 200 is a function within web browser 150, and the processes of program 200 occur automatically (i.e., without user intervention) during operation of web browser 150 as initiated by program 200. The dynamic code snippet elements provide scripting support. The variables enable dialog between program 200, through server 120, graphical user interface 130, web browser 150, and biomimetic chip 155.

Figure 2:
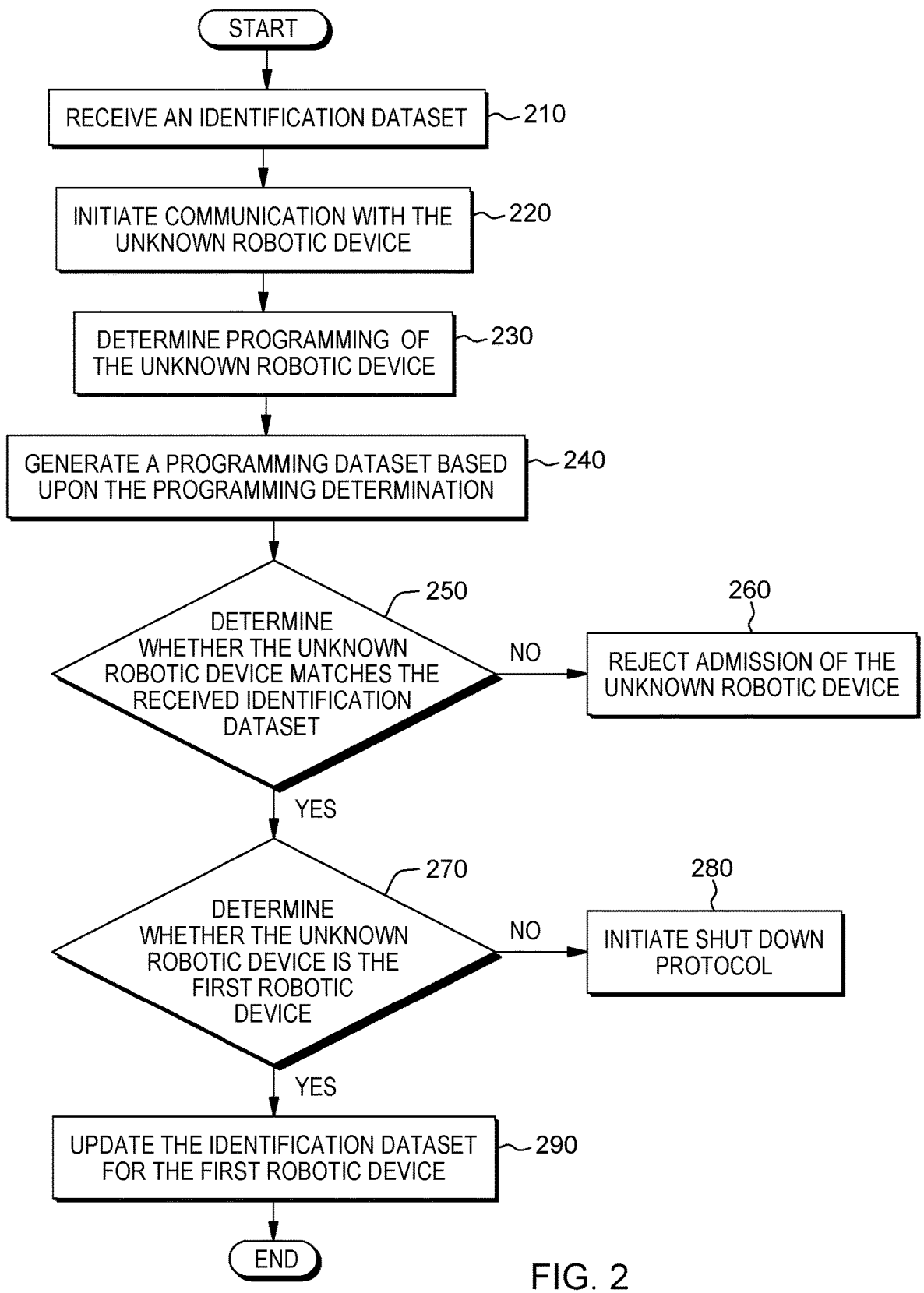
FIG. 2 is a flowchart depicting operational steps of program 200, a program for identifying a robotic device, in accordance with an embodiment of the present invention.

FIG. 2 is a flowchart depicting program 200, a program for identifying a robotic device, in accordance with an embodiment of the present invention.

In step 210, program 200 receives an identification dataset. In an embodiment, program 200 receives an identification dataset from the output of a neural network, not shown, that includes a historical dataset for a first, unknown robotic device. Program 200 is capable of receiving multiple identification datasets for different constituent parts of the same robot, and an identification dataset for the robot itself. In an example, program 200 simultaneously receives five datasets for four different surgical arms, and the body of the robot, that are attached to the same surgical robot. The received datasets are particular to individual arms, the individual robot, and are not fungible. In this example, received identification dataset 1 corresponds to surgical arm one, while received identification dataset two corresponds to surgical arm two, received identification dataset three corresponds to surgical arm three, and received identification dataset four corresponds to surgical arm four. Received identification dataset five corresponds to the main body of the robot.

In another embodiment, program 200 receives an identification dataset from one robot. In an example, program 200 receives an identification dataset as output from a neural network, that is not depicted, from the body of one robot. The identification dataset corresponds to the body of the robot since this robot does not have arms, or other functional components. In another embodiment, program 200 receives an identification dataset for two arms that are not physically connected to the body of a robot, and the body of a robot that is not in physical proximity to the arms that constitute the robot.

Figure 3:
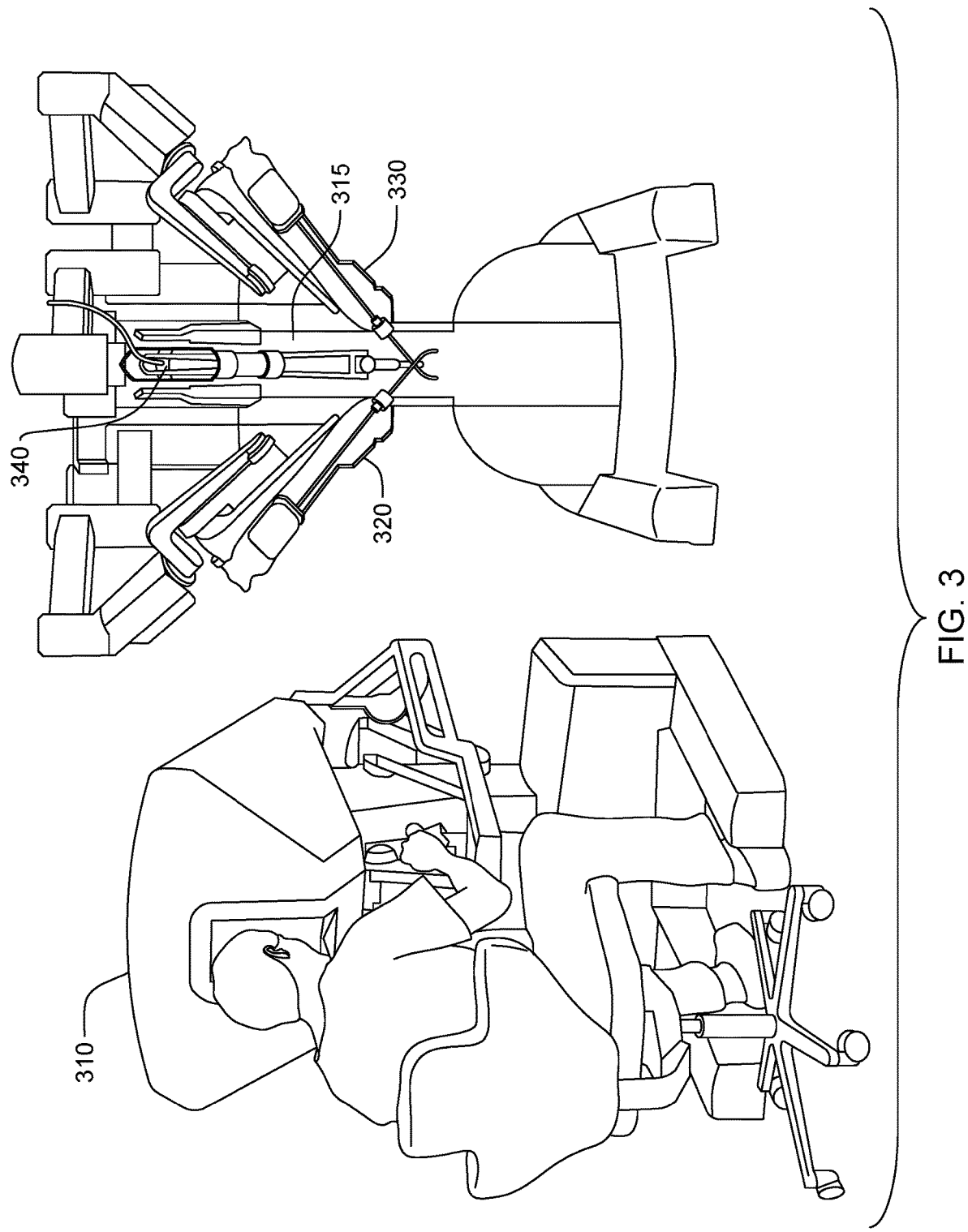
FIG. 3 illustrates an example of the program identifying a robotic device, in accordance with an embodiment of the invention.

FIG. 3 illustrates an example of program 200 initiating communication with an unknown robotic device, in accordance with an embodiment of the present invention. In this embodiment, program 200 operates on a computing device, 310, associated with the robotic device and initiates communication with an unknown robotic device 315 where surgical robotic arms 320, 330, and 340 are attached to the unknown robotic device 315. Program 200 is capable of initiating communication with unknown robotic device 315 independent of, and in concert with, one, two, or all of surgical robotic arms 320, 330, and 340. Surgical robotic arms 320, 330, and 340 are capable of performing a signature movement that is uniquely associated with the individual appendage.

In step 220, program 200, through computing device 310, communicates with the unknown robotic device 315 that 320, 330, and 340 are attached. Program 200 is capable of initiating, and program 200 is receptive to, active communication and passive communication individually with the unknown robotic device 315 and the unknown surgical robotic arms 320, 330, and 340. In an embodiment, program 200 obtains an audio signal from the unknown robotic device 315, and the unknown surgical robotic arms 320, 330, and/or 340 and processes the audio signal to obtain an audio profile each or all of the unknown surgical robotic arms of the unknown robotic device. In an example, program 200 is receptive to an analogue or digital information signal from the individual components 320, 330 and 340 of an unknown robotic device 315. In this example, program 200 initiates communication with an unknown robotic device through the digital representation of the pressure wave-form as binary numbers to permit processing of the signal. To aid in actively initiating communication with one or more components of the unknown robotic device, program 200 is capable of data compression, enhancement through equalization, filtering, and echo removal and addition.

In another embodiment, program 200 initiates the modeling of biomimetic signature profile of the unknown surgical arms 320, 330, and 340. In an example, program 200 utilizes device signature meta knowledge to communicate with 320, 330, and 340. Program 200 actively communicates to the unknown 320, 330, and 340 to request 320, 330, and 340 to model a signature profile of 320, 330, and 340 stored on one or more databases. In an example, program 200 initiates communication with 320, 330, and 340, three individual surgical robotic arms, attached to one body. In this example, each individual arm performs a signature movement that is uniquely associated with the individual appendage. One individual arm may move up three times as corresponding to the signature movement. Another individual arm may rotate clockwise in a repetitive fashion until a command is received by the robotic arm.

In another embodiment, program 200 requests a collection of knowledge priors from the unknown robotic device 315 based on the historical dataset received in step 210 to determine the programming of the unknown robotic device. In an example, program 200 requests prior device identification response knowledge collection through communicating with an unknown robotic device.

In another embodiment, program 200 performs an optical scan of an unknown robotic device 315 to produce an optical scan image of two individual robotic arms. Program 200 is capable of determining that the image may not be an exact replication, but that the scanned image meets a threshold likeness standard. The optical scan of the robotic arms works similar to the optical scan of a human iris. The optical scan searches for a verifiable, identification marker such as an imprinted barcode or combination of barcodes that are particular to the individual robotic arm being optically scanned. The optical scan searches for a match to the physical profile of the robotic device using a light beam to scan the robotic device for nuances of the physical profile of the robotic device that are unique to the specific robotic device. The optical scan can also use a light beam, to analyze a barcode that corresponds to the identification profile of a robotic device wherein the identification profile is stored on one or more databases. Program 200 is capable of performing both an optical scan of the robotic device in combination with scanning a barcode to communicate with the unknown robotic device.

In another embodiment, program 200 initiates communication with a robotic device through analytic and interrogative reasoning programming. In this example, program 200 can actively, or passively, initiate communication with an unknown robotic device 315 by performing an action, observing the action of the unknown robotic device, and searching for changes in the unknown robotic device as a consequence of the initiated communication with the unknown robotic device.

In other embodiments, program 200 is capable of initiating communication with the unknown robotic device 315 through other objective and direct methods of identification such as torque sensing, movement pattern identification for the body of the robot, and movement pattern identification of one or more individual extremities of a robotic device.

In step 230, program 200 determines the programming of the unknown robotic device. In an embodiment, program 200 interrogates the unknown robotic device 315 to determine the analytic and reasoning programming of the unknown robotic device. In this embodiment, program 200 determines the programming of the unknown robotic device 315 through an ongoing persistent and continuous revalidation. Step 230 is a continuous process to revalidate the unknown robotic device 315. In an example, program 200 constantly monitors surgical robotic arms 320, 330, and 340 due to the fact that the surgical robotic arms are highly susceptible to being hacked by outside entities. In this example, program 200 performs a malfunction check on the surgical robotic arms to determine whether the programming corresponds to the programming stored on one or more databases as corresponding to the surgical robotic arms 320, 330, and 340. In this example, program 200 instructs the surgical robotic arms to cease the action it is performing and respond to the instruction at five minute intervals. Program 200 utilizes the instruct and observe action of the surgical robotic arms as a persistent way of making sure that the surgical robotic arm is not malfunctioning or the surgical robotic arm has not been hacked.

In step 240, program 200 generates a program data set based upon the determined programming of the unknown robotic device 315. In an embodiment, program 200 generates a programming dataset based upon the interrogation and observed communication of an unknown robotic device 315. In an example, program 200 utilizes three active, distinct signals of three individual surgical robotic arms 320, 330, and 340 attached to a robotic device through a series instructed movements to generate a programming dataset. The generated programming dataset is used to generate three identification datasets for the three unknown surgical robotic arms 320, 330, and 340.

In another embodiment, program 200 generates a programming dataset utilizing a passive identification process. In an example, program 200 generates an unknown robotic device identification dataset through recording and analyzing the gate and normal operating sounds of an unknown robotic device 315. In this example, the unknown robotic device identification dataset is generated utilizing the characteristic gate and normal operating sounds.

In an embodiment, program 200 compares the optical scan image, the audio signal profile, the biomimetic signature profile, the received knowledge priors, and/or the programming dataset to generate an unknown robotic device dataset. In an example, program 200 combines the accumulated evidence from step 220 and step 230 to generate an unknown surgical robotic arm identification dataset. In this example, program 200 generates a programming dataset for the surgical robotic arms in individual and in combination, based upon the optical scanned image of a barcode, the audio signal profile of the normal operating sounds of the surgical robotic arm, the biomimetic signature profile of the signature movements of the surgical robotic arms, the received knowledge priors of the most recent activity of the surgical robotic arms, to generate an identification dataset for the surgical robotic arms individually and in combination.

In decision step 250, program 200 determines whether the unknown robotic device identification dataset matches the received identification dataset of the first robotic device. In an embodiment, program 200 determines that the unknown robotic device is the first robotic device to identify with a high level of certainty that the particular robotic device is the robotic device that the robotic device asserts to be. In an example, the programming dataset of a surgical robotic arm evolves over time based upon the movements of the surgical robotic arm. In this example program 200 utilizes the information and evidence accumulated in step 240, with respect to the determined programming dataset of a surgical robotic arm, to determine if the surgical robotic arm contains the same identification data set received in step 210. Program 200 determines whether the surgical robotic arm matches the received identification dataset of the surgical robotic arm.

In step 260, program 200 rejects admission of the unknown robotic device. More specifically, in response to determining that the unknown robotic device does not match the received identification dataset (decision step 250, "no" branch) program 200 rejects admission of the unknown robotic device. In an embodiment, program 200 attempts to confirm the identification of an unknown robotic device and is unsuccessful. In an example, program 200 attempts to verify that an unknown surgical robotic arm matches the received identification dataset of a surgical robotic arm. In this example, program 200 determines that that the unknown surgical robotic arm and the received identification dataset of a surgical robotic arm do not match. Program 200 rejects admission of the unknown robotic device through activating an alarm to deny admission of the surgical robotic arm into an operating room.

In decision step 270, program 200 determines whether the unknown robotic device is the first robotic device (decision step 250, "yes" branch). In an embodiment, program 200 utilizes the accumulated evidence, in step 240, of an unknown robotic device, to positively identify and determine that the unknown robotic device is the first robotic device correlated with the received identification dataset in step 210. Program 200 persistently revalidates and confirms the identification of an unknown robotic device constantly. It is possible that Program 200 initially determines, based upon the positive identification determination made in decision step 250, that the unknown robotic device is the first robotic device and due to the evolving nature of the programming dataset, Program 200 determines that the same robotic device that was previously positively identified no longer is the previously positively identified robotic device.

In another embodiment, Program 200 incorporates a tolerance factor in determining whether the unknown robotic device is the first robotic device. In an example, Program 200, utilizing a tolerance factor of 90%, determines whether a robotic device containing ten individual surgical robotic arms are properly identified in order to validate the ten individual surgical robotic arm and admit the robotic device. Program 200 utilizes a tolerance factor of 90% to determine whether the unknown surgical robotic arms receive a positive identification. At least nine of the ten surgical robotic arms must match the received identification datasets with the unknown surgical robotic arms. In this example, nine out of ten surgical robotic arms were properly validated as matching the received identification for the surgical robotic arms. Program 200 determines that the unknown surgical robotic arms are the first surgical robotic arms and receive a positive identification. The entire robot, and the ten surgical robotic arms, with one surgical robotic arm failing the biomimetic identification device communication response, are admitted.

In another example, Program 200, utilizing a tolerance factor of 90%, determines that eight out of ten surgical robotic arms were properly validated as matching the received identification for the surgical robotic arms. Program 200 in unable to determine that the two individual unknown surgical robotic arms are properly validated as were the first eight surgical robotic arms. In this instance, the entire robotic device does not receive a positive identification. The entire robot, and the ten surgical robotic arms, with two surgical robotic arms failing the biomimetic identification device communication response, are not admitted.

In step 280, program 200 initiates shut down protocol (decision step 270, "no" branch). In response to determining that the unknown robotic device is not the first robotic device, Program 200 initiates a shutdown protocol of the unknown robotic device. In an example, Program 200 determines that the previously positive biomimetic identification of a surgical robotic arm no longer correlates with the proper biomimetic identification. In this example, Program 200 performs a revalidation, steps 210-250, of five surgical robotic arms. Based upon an established tolerance factor, 80%, of the surgical robotic arms not working properly or not being positively identified, Program 200, because two out of five arms are not working, exceeding the tolerance factor of 80%, initiates a shutdown protocol of all five surgical robotic arms. In another example, four out of the five arms are positively identified, and moving consistent with their proper biomimetic identification consistent with their evolved programming dataset as generated in step 240, Program 200 continues with the operation using the surgical robotic arms and does not initiate a shut down. The tolerance factor in this example is not exceeded.

In step 290, program 200 updates the identification dataset for the first robotic device (decision step 270) "yes" branch. In response to determining that the unknown robotic device matches the received identification dataset, from step 210, program 200 updates the identification dataset for the first robotic device with additional data. In an embodiment, the programming dataset constantly evolves due to cognitive robotic regression based priors. In an example, Program 200 enhances the efficiency of identifying robotic devices based upon the accumulated knowledge established from prior robotic identifications.

Figure 4:
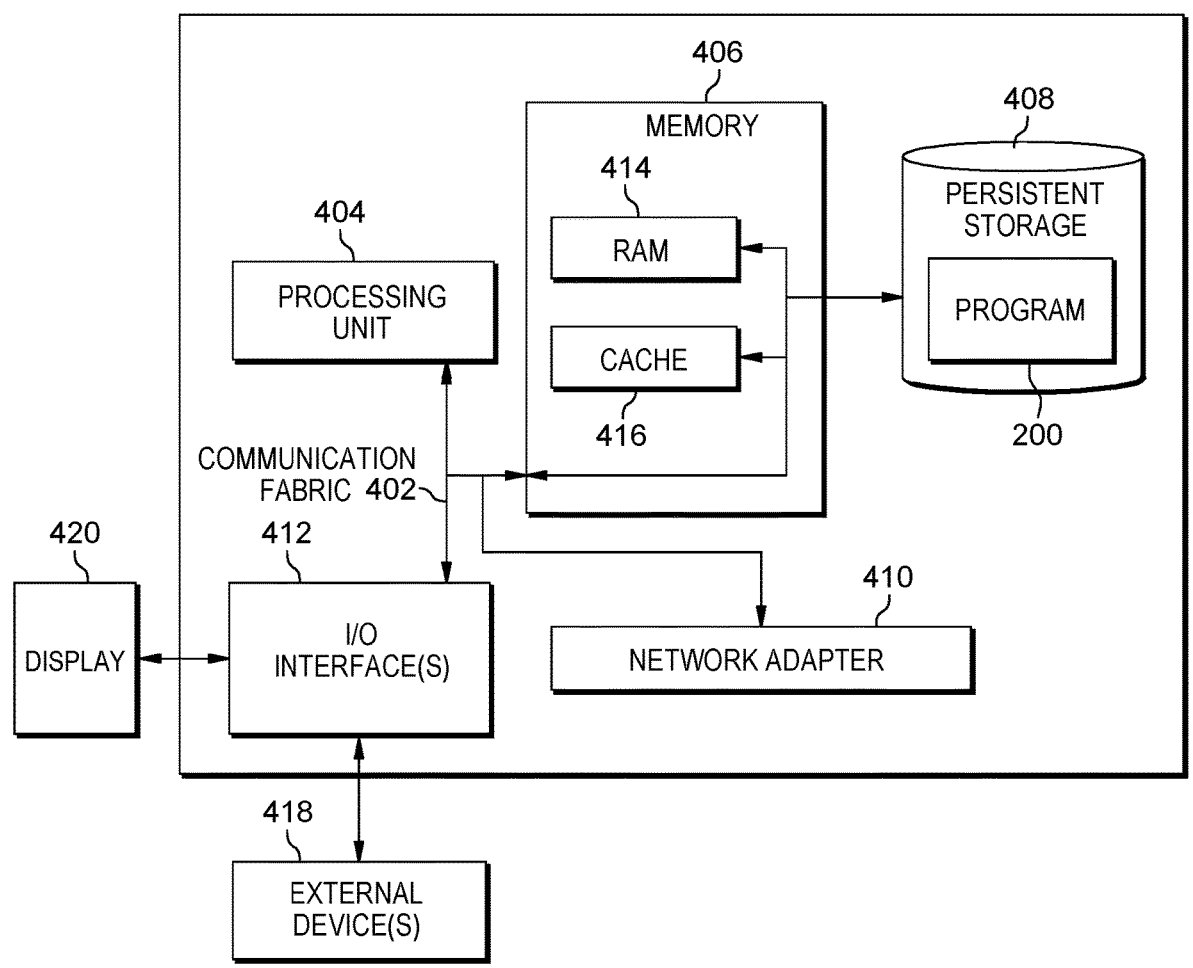
FIG. 4 is a block diagram of components of a computer system, such as the server computer of FIG. 1, in an embodiment in accordance with the present invention.

FIG. 4 depicts a block diagram of components of server 120, in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

Server 120 includes communications fabric 402, which provides communications between cache 416, memory 406, persistent storage 408, communications unit 410, and input/output (I/O) interface(s) 412. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses or a crossbar switch.

Memory 406 and persistent storage 408 are computer readable storage media. In this embodiment, memory 406 includes random access memory (RAM). In general, memory 406 can include any suitable volatile or non-volatile computer readable storage media. Cache 416 is a fast memory that enhances the performance of computer processor(s) 404 by holding recently accessed data, and data near accessed data, from memory 406.

Program 200 may be stored in persistent storage 408 and in memory 406 for execution by one or more of the respective computer processors 404 via cache 416. In an embodiment, persistent storage 408 includes a magnetic hard disk drive. Alternatively, or in addition to a magnetic hard disk drive, persistent storage 408 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 410, in these examples, provides for communications with other data processing systems or devices. In these examples, communications unit 410 includes one or more network interface cards. Communications unit 410 may provide communications through the use of either or both physical and wireless communications links. Program 200 may be downloaded to persistent storage 408 through communications unit 410.

I/O interface(s) 412 allows for input and output of data with other devices that may be connected to server 120. For example, I/O interface 412 may provide a connection to external devices 418 such as a keyboard, keypad, a touch screen, and/or some other suitable input device. External devices 418 can also include portable computer readable storage media such as, for example, thumb drives, portable optical or magnetic disks, and memory cards. Software and data used to practice embodiments of the present invention, e.g., program 200, can be stored on such portable computer readable storage media and can be loaded onto persistent storage 408 via I/O interface(s) 412. I/O interface(s) 412 also connect to a display 420.

Display 420 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for identifying a robotic device, the method comprising:

receiving, by one or more processors, an authentication request for an unknown robotic device asserting to be a first robotic device;

receiving, by one or more processors, a first identification dataset for the first robotic device from an output of a neural network;

issuing, by one or more processors, an identification action to the unknown robotic device;

generating, by one or more processors, a second identification dataset for the unknown robotic device based upon a response to the identification action received from the unknown robotic device;

incorporating, by one or more processors, a tolerance factor for determining whether the unknown robotic device is the first robotic device, the tolerance factor corresponding to a number of matches between the first identification dataset and the second identification dataset;

based on the number of matches between the first identification dataset and the second identification dataset agreeing with the tolerance factor, determining, by one or more processors, that the unknown robotic device is the first robotic device; and authenticating, by one or more processors, the unknown robotic device in response to determining that the unknown robotic device is the first robotic device.

2. The method of claim 1, wherein the generating the second identification dataset further comprises:
obtaining, by one or more processors, an audio signal from the unknown robotic device;
executing, by one or more processors, an audio signaling processing on the audio signal; and
generating, by one or more processors, an audio signal profile of the unknown robotic device.

3. The method of claim 1 further comprising:
receiving, by one or more processors, a signature biomimetic input from the first robotic device;
determining, by one or more processors, a corresponding signature biomimetic output;
modeling, by one or more processors, the corresponding signature biomimetic output, and
wherein generating the second identification dataset is based on the corresponding signature biomimetic output of the unknown robotic device.

4. The method of claim 1, wherein authenticating the unknown robotic device in response to determining that the unknown robotic device is the first robotic device further comprises:
initiating, by one or more processors, communication with the first robotic device; and
in response to determining the unknown robotic device is the first robotic device, updating, by one or more processors, the identification dataset for the first robotic device.

5. The method of claim 1, wherein authenticating the unknown robotic device in response to determining that the unknown robotic device is the first robotic device further comprises:
executing, by one or more processors, an optical scanning;
generating, by one or more processors, an optical scan image of the unknown robotic device; and
determining, by one or more processors, that the generated unknown robotic device optical scan image matches an optical scan image from one or more databases.

6. The method of claim 1, wherein authenticating the unknown robotic device in response to determining that the unknown robotic device is the first robotic device further comprises:
initiating, by one or more processors, a request for knowledge priors from the first robotic device, wherein the knowledge priors relates to previously stored identification results of the first robotic device;
receiving, by one or more processors, knowledge priors from the first robotic device;
determining, by one or more processors, that the knowledge priors match the knowledge priors on one or more databases; and
granting, by one or more processors, access to the first robotic device to one or more restricted areas.

7. The method of claim 1, wherein authenticating the unknown robotic device in response to determining that the unknown robotic device is the first robotic device further comprises:
initiating, by one or more processors, an interrogation of the unknown robotic device asserting to be the first robotic device;
interrogating, by one or more processors, the unknown robotic device asserting to be the first robotic device;
determining, by one or more processors, that the unknown robotic device asserting to be the first robotic device responds to the interrogation in a manner that corresponds to data on one or more databases; and
admitting, by one or more processors, the first robotic device to one or more restricted areas.

8. The method of claim 1 further comprising:
in response to determining that the first identification dataset does not match the second identification dataset, initiating, by one or more processors, a shutdown protocol.

9. The method of claim 1 wherein responsive to determining the unknown robotic device is the first robotic device further comprises:
determining, by one or more processors, a continuous monitoring for the first robotic device; and
monitoring, by one or more processors, the first robotic device.

10. A computer program product identifying a robotic device, the computer program product comprising:
one or more computer readable tangible storage media and program instructions stored on at least one of the one or more computer readable storage media, the program instructions readable/executable by one or more computer processors and further comprising:
program instructions to receive an authentication request for an unknown robotic device asserting to be a first robotic device;
program instructions to receive a first identification dataset for the first robotic device from an output of a neural network;
program instructions to issue an identification action to the unknown robotic device;
program instructions to generate a second identification dataset for the unknown robotic device based upon a response to the identification action received from the unknown robotic device;
program instructions to incorporate a tolerance factor for determining whether the unknown robotic device is the first robotic device, the tolerance factor corresponding to a number of matches between the first identification dataset and the second identification dataset;
based on the number of matches between the first identification dataset and the second identification dataset agreeing with the tolerance factor, program instructions to determine, that the unknown robotic device is the first robotic device; and
program instructions to authenticate the unknown robotic device in response to determining that the unknown robotic device is the first robotic device.

11. The computer program product of claim 10, wherein the generating the second identification dataset further comprises program instructions, stored on the one or more computer readable storage media, which when executed by a processor, cause the processor to:
obtain an audio signal from the robotic device;
execute an audio signaling processing on the audio signal; and
generate an audio signal profile of the unknown robotic device.

12. The computer program product of claim 10, further comprising program instructions, stored on the one or more computer readable storage media, which when executed by a processor, cause the processor to:
receive a signature biomimetic input from the first robotic device;
determine a corresponding signature biomimetic output;

model the corresponding signature biomimetic output; and wherein generating the second identification dataset is based on the corresponding signature biomimetic output of the unknown robotic device.

13. The computer program product of claim 10, wherein authenticating the unknown robotic device in response to determining that the unknown robotic device is the first robotic device further comprises program instructions, stored on the one or more computer readable storage media, which when executed by a processor, cause the processor to:
    initiating communication with the first robotic device; and
    in response to determining the unknown robotic device is the first robotic device, update the identification dataset for the first robotic device.

14. The computer program product of claim 10, wherein authenticating the unknown robotic device in response to determining that the unknown robotic device is the first robotic device further comprises program instructions, stored on the one or more computer readable storage media, which when executed by a processor, cause the processor to:
    execute an optical scanning;
    generate an optical scan image of the unknown robotic device; and
    determine that the generated unknown robotic device optical scan image matches an optical scan image from one or more databases.

15. The computer program product of claim 10, wherein authenticating the unknown robotic device in response to determining that the unknown robotic device is the first robotic device further comprises program instructions, stored on the one or more computer readable storage media, which when executed by a processor, cause the processor to:
    initiate a request for knowledge priors from the first robotic device, wherein the knowledge prior relates to previously stored identification results of the first robotic device;
    receive knowledge priors from the first robotic device;
    determine that the knowledge priors match the knowledge priors on one or more databases; and
grant access to the first robotic device to one or more restricted areas.

16. The computer program product of claim 10, further comprising program instructions, stored on the one or more computer readable storage media, which when executed by a processor, cause the processor to:
    initiate an interrogation of the unknown robotic device asserting to be the first robotic device;
    interrogate the unknown robotic device asserting to be the first robotic device;
    determine that the unknown robotic device asserting to be the first robotic device responds to the interrogation in a manner that corresponds to data on one or more databases; and
    admit the first robotic device to one or more restricted areas.

17. The computer program product of claim 10, further comprising program instructions, stored on the one or more computer readable storage media, which when executed by a processor, cause the processor to:
    in response to determining that the first identification dataset for an unknown robotic device asserting to be the first robotic device does not match the first robotic device programming dataset, initiate a shutdown protocol.

18. The computer program product of claim 10, wherein responsive to determining the unknown robotic device is the first robotic device further comprises program instructions, stored on the one or more computer readable storage media, which when executed by a processor, cause the processor to:
    determine a continuous monitoring for the first robotic device; and
    monitor the first robotic device.

19. A computer system comprising:
    one or more computer processors;
    one or more computer readable storage media; and
    program instructions stored on the computer readable storage media for execution by at least one of the one or more computer processors, the program instructions comprising:
    program instructions to receive an authentication request for an unknown robotic device asserting to be a first robotic device;
    program instructions to receive a first identification dataset for the first robotic device from an output of a neural network;
    program instructions to issue an identification action to the unknown robotic device;
    program instructions to generate a second identification dataset for the unknown robotic device based upon a response to the identification action received from the unknown robotic device;
    program instructions to incorporate a tolerance factor for determining whether the unknown robotic device is the first robotic device, the tolerance factor corresponding to a number of matches between the first identification dataset and the second identification dataset;
    based on the number of matches between the first identification dataset and the second identification dataset agreeing with the tolerance factor, program instructions to determine, that the unknown robotic device is the first robotic device; and
    program instructions to authenticate the unknown robotic device in response to determining that the unknown robotic device is the first robotic device.

20. The computer system of claim 19, wherein the generating the second identification dataset further comprises program instructions, stored on the one or more computer readable storage media, which when executed by a processor, cause the processor to:
    obtain an audio signal from the robotic device;
    execute an audio signaling processing on the audio signal; and
    generate an audio signal profile of the unknown robotic device.

21. The computer system of claim 19, further comprising program instructions, stored on the one or more computer readable storage media, which when executed by a processor, cause the processor to:
    receive a signature biomimetic input from the first robotic device;
    determine a corresponding signature biomimetic output;
    model the corresponding signature biomimetic output; and
    wherein generating the second identification dataset is based on the corresponding signature biomimetic output of the unknown robotic device.

22. The computer system of claim 19, wherein authenticating the unknown robotic device in response to determining that the unknown robotic device is the first robotic device further comprises program instructions, stored on the one or more computer readable storage media, which when executed by a processor, cause the processor to:

initiating communication with the first robotic device; and in response to determining the unknown robotic device is the first robotic device, update the identification dataset for the first robotic device.

23. The computer system of claim 19, wherein authenticating the unknown robotic device in response to determining that the unknown robotic device is the first robotic device further comprises program instructions, stored on the one or more computer readable storage media, which when executed by a processor, cause the processor to:

execute an optical scanning;

generate an optical scan image of the unknown robotic device; and determine that the generated unknown robotic device optical scan image matches an optical scan image from one or more databases.

24. The computer system of claim 19, wherein authenticating the unknown robotic device in response to determining that the unknown robotic device is the first robotic device further comprises program instructions, stored on the one or more computer readable storage media, which when executed by a processor, cause the processor to:

initiate a request for knowledge priors from the first robotic device, wherein the knowledge prior relates to previously stored identification results of the first robotic device;

receive knowledge priors from the first robotic device;

determine that the knowledge priors match the knowledge priors on one or more databases; and grant access to the first robotic device to one or more restricted areas.

25. The computer system of claim 19, further comprising program instructions, stored on the one or more computer readable storage media, which when executed by a processor, cause the processor to:

initiate an interrogation of the unknown robotic device asserting to be the first robotic device;

interrogate the unknown robotic device asserting to be the first robotic device;

determine that the unknown robotic device asserting to be the first robotic device responds to the interrogation in a manner that corresponds to data on one or more databases; and admit the first robotic device to one or more restricted areas.

* * * * *